(12) United States Patent
Winowiski et al.

(10) Patent No.: US 7,901,701 B2
(45) Date of Patent: Mar. 8, 2011

(54) METHODS FOR PRODUCING DRIED PESTICIDE COMPOSITIONS

(75) Inventors: Thomas S. Winowiski, Mosinee, WI (US); Stuart E. Lebo, Ringle, WI (US); Scott E. Davis, Schofield, WI (US); Stig Are Gundersen, Torp (NO)

(73) Assignee: Lignotech USA, Inc., Rothschild, WI (US)

( * ) Notice: Subject to any disclaimer, the term of this patent is extended or adjusted under 35 U.S.C. 154(b) by 122 days.

(21) Appl. No.: 11/926,535

(22) Filed: Oct. 29, 2007

(65) Prior Publication Data

US 2009/0110707 A1   Apr. 30, 2009

(51) Int. Cl.
*A01N 25/00* (2006.01)
*A01N 25/12* (2006.01)
*A01N 33/18* (2006.01)
*A01N 37/18* (2006.01)
*A01N 43/54* (2006.01)
*A01N 43/56* (2006.01)
*A01N 43/88* (2006.01)

(52) U.S. Cl. ......... 424/405; 504/220; 504/300; 504/341; 504/347; 504/358; 514/112; 514/122; 514/132; 514/141; 514/229.2; 514/269; 514/403; 514/520; 514/531; 514/619; 514/777

(58) Field of Classification Search .................. 424/405
See application file for complete search history.

(56) References Cited

U.S. PATENT DOCUMENTS

| | | | |
|---|---|---|---|
| 3,726,850 A | 4/1973 | Detroit | |
| 3,986,979 A | 10/1976 | Moorer et al. | |
| 3,992,532 A | 11/1976 | Dimitri | |
| 4,184,866 A * | 1/1980 | Dellicolli et al. | 504/366 |
| 4,244,728 A | 1/1981 | DelliColli et al. | |
| 4,244,729 A | 1/1981 | DelliColli et al. | |
| 4,381,194 A * | 4/1983 | DelliColli et al. | 504/103 |
| 4,666,522 A * | 5/1987 | Hollis et al. | 106/249 |
| 4,732,572 A | 3/1988 | Dilling | |
| 4,751,247 A | 6/1988 | Dilling et al. | |
| 4,797,157 A | 1/1989 | Dilling et al. | |
| 4,952,415 A | 8/1990 | Winowiski et al. | |
| 4,957,748 A | 9/1990 | Winowiski | |
| 5,023,091 A | 6/1991 | Winowiski | |
| 5,032,164 A | 7/1991 | Sanford et al. | |
| 5,246,739 A | 9/1993 | Lin | |
| 5,281,434 A | 1/1994 | Winowiski et al. | |
| 5,446,133 A | 8/1995 | Detroit | |
| 5,529,772 A | 6/1996 | Lebo, Jr. | |
| 5,552,149 A | 9/1996 | Lebo, Jr. et al. | |
| 5,663,425 A | 9/1997 | Detroit et al. | |
| 5,668,183 A | 9/1997 | Leuenberger | |
| 5,688,999 A | 11/1997 | Lebo, Jr. et al. | |
| 5,789,001 A | 8/1998 | Klopfenstein et al. | |
| 5,925,743 A | 7/1999 | Detroit | |
| 5,939,089 A | 8/1999 | Wirtz et al. | |
| 5,994,266 A | 11/1999 | Hobbs et al. | |
| 6,019,835 A | 2/2000 | Chatterji et al. | |
| 6,113,974 A | 9/2000 | Winowiski et al. | |
| 6,238,475 B1 | 5/2001 | Gargulak et al. | |
| 6,346,347 B1 | 2/2002 | McNally et al. | |
| 6,372,037 B1 | 4/2002 | Lebo, Jr. et al. | |
| 6,455,471 B1 * | 9/2002 | Gubelmann-Bonneau et al. | 504/133 |
| 6,558,461 B2 | 5/2003 | Lebo, Jr. et al. | |
| 6,664,002 B2 | 12/2003 | McNally et al. | |
| 6,906,007 B2 * | 6/2005 | Fischer et al. | 504/292 |
| 7,303,707 B2 | 12/2007 | Rafferty et al. | |
| 7,426,948 B2 * | 9/2008 | Richardson et al. | 144/364 |
| 2002/0009787 A1 * | 1/2002 | Becker et al. | 435/183 |
| 2002/0056405 A1 | 5/2002 | Lebo, Jr. et al. | |
| 2004/0038094 A1 | 2/2004 | Klenk et al. | |
| 2005/0038094 A1 | 2/2005 | Warrington | |
| 2007/0161512 A1 | 7/2007 | Smith et al. | |
| 2008/0113920 A1 * | 5/2008 | Yang et al. | 514/22 |

OTHER PUBLICATIONS

Nedosvitii, V.P.; Antonov, G.I.; Vinogradova, M.A.; and Dimakova, L.K. "Use of Lignosulfonates as binders in refractories." Submitted Nov. 1, 1993. Refractories: vol. 35, No. 5, 1994, pp. 145-150.*
Carmen G. Boeriu, Dominique Bravo, Richard J.A. Gosselink, Jan E.G. van Dam. "Characterisation of structure-dependent functional properties of lignin with infrared spectroscopy." Industrial Crops and Products, 20, (2004), 205-218.*
"Review of current and future softwood kraft lignin process chemistry." Fadi S. Chakar, Arthur J. Ragauskas. Industrial Crops and Products 20 (2004) 131-141.*
"Molecular Weights of Lignosulfonates", Technical Bulletin No. 008, Borregaard LignoTech, May 2004.

* cited by examiner

*Primary Examiner* — Richard Schnizer
*Assistant Examiner* — Audrea J Buckley
(74) *Attorney, Agent, or Firm* — Andrus, Sceales, Starke & Sawall, LLP

(57) ABSTRACT

Disclosed are compositions and methods related to powder and granular emulsifiable concentrate pesticide formulations. As disclosed, emulsions from non-aqueous based liquid or solvent soluble pesticide actives may be prepared using a high purity, high molecular weight sulfonated lignin as the emulsion stabilizer. The resulting emulsions may then be dried to obtain a powder or granular emulsion concentrate where the high molecular weight sulfonated lignin acts as a solid matrix for the pesticide active. The powder or granular emulsifiable concentrate formulations thus formed have high loading rates, good storage properties and are easily reconstituted when added to water.

31 Claims, No Drawings

METHODS FOR PRODUCING DRIED PESTICIDE COMPOSITIONS

BACKGROUND

The present invention relates to pesticide compositions and methods for producing pesticide compositions. The disclosed compositions may include granular pesticide compositions and powder pesticide compositions which are prepared directly from liquid emulsions of the pesticide in solutions of lignosulfonate and which in turn may be reconstituted in water into stable emulsions.

Many pesticides are hydrophobic organic compounds. Some hydrophobic pesticide compounds have a relative low melting point, such that they exist as a liquid at room temperature. Other hydrophobic pesticide compounds having a higher melting point may be dissolved in an organic solvent to obtain a pesticide solution. In order to disperse the pesticide liquid or solution in water for easy application, the pesticide may be formulated as a water-dispersible emulsifiable concentrate. This process typically requires an emulsifying agent, which will cause an emulsion to form spontaneously when the concentrate is added to water.

Processed lignin is obtained as a by-product of wood pulping reactions and has been shown to be useful for a variety of commercial applications. For example, alkali soluble lignin has been used as a dispersing agent. U.S. Pat. No. 3,726,850 discloses the use of an alkali soluble, ozone-treated lignin product, which is essentially free of organically bound sulfur, as a dispersing agent for clays, dyestuffs, pesticides, carbon black and other materials. The '850 patent contrasts the use of alkali soluble, ozone-treated lignin material as dispersing agents with lignosulfonate dispersing agents. Furthermore, the '850 patent does not indicate whether the disclosed formulations are suitable for preparing granular pesticide formulations that may be reconstituted as emulsions.

U.S. Pat. No. 4,666,522 discloses the use of lignosulfonate products for preparing emulsions of waxes, oils, fats, asphalts, and mixtures thereof. However, the '522 patent does not disclose the use of high purity, high molecular weight lignosulfonates as emulsifying agents for hydrophobic, low melting point pesticides. Furthermore, the '522 patent indicates that a stable emulsion cannot be prepared unless the lignosulfonate concentration is 45-65%. The '522 patent also does not indicate whether the disclosed formulations are suitable for preparing granular pesticide formulations that may be reconstituted as emulsions.

U.S. Pat. No. 5,668,183 discloses the use lignosulfonate products for dispersing fat-soluble substances. However, the '183 patent does not disclose the use of high purity, high molecular weight lignosulfonates as emulsion stabilizers for hydrophobic, low melting point pesticides. The '183 patent indicates that suitable lignosulfonate products consist of 40-90% lignosulfonic acid, or its salts, and include various amounts of hygroscopic agents such as saccharides, ash, carbohydrates, acetates, formates, resins, etc. Lignosulfonate products that have relatively high sugar content also are taught as being suitable for the methods of the '183 patent. The '183 patent does not indicate that high purity lignosulfonates having low sugar content are desirable or even suitable for the disclosed methods. Furthermore, the '183 patent does not indicate whether the disclosed formulations are suitable for preparing granular pesticide formulations that may be reconstituted as emulsions.

Safer and more environmentally friendly emulsion stabilizers and carriers for pesticides are needed. Disclosed herein are high purity, high molecular weight lignosulfonate materials for preparing stable, dispersible pesticide emulsions. The prepared emulsions may be dried or granulated to obtain powder or granular pesticide formulations, which in turn, may be reconstituted with water to obtain stable, dispersible emulsions. The disclosed pesticide formulations exhibit many desirable characteristics such as stability, flowability, dissolvability, and low hygroscopicity.

SUMMARY

Disclosed are pesticide compositions and methods for producing pesticide compositions. The disclosed compositions may include granular compositions and powder compositions prepared directly from emulsions. The granular compositions and powder compositions disclosed herein can be stored for significant periods of time after which they may be reconstituted into stable emulsions for application in the field, yard, or garden.

The disclosed compositions may include granular compositions and powder compositions prepared from emulsions made by combining a non-aqueous based liquid or solvent soluble pesticide active with an aqueous solution comprising a high purity, high molecular weight sulfonated lignin and optionally a diluent such as lactose. The sulfonated lignin may stabilize the emulsion once it has been formed (e.g., by mechanical shear or ultrasonication). When the emulsion is dried or granulated, the high purity, high molecular weight sulfonated lignin may provide an inert, water soluble matrix for the pesticide active. When the dried or granulated emulsion is combined with an aqueous solution, the high purity, high molecular weight sulfonated lignin will dissolve and further may function as an emulsion stabilizer for the reconstituted pesticide active.

In some embodiments, the disclosed compositions may include dried or granulated emulsions. The disclosed emulsions may be prepared by a method that includes: (a) preparing an aqueous lignosulfonate solution by dissolving a lignosulfonate material in water or an aqueous solution, where the lignosulfonate material comprises at least about 90% (w/w) lignosulfonic acid, or its salts, (preferably at least about 95% (w/w) lignosulfonic acid or its salts) and the lignosulfonate has an average molecular weight of about 20 kDa to about 100 kDa (preferably about 40 kDa to about 60 kDa); (b) combining the aqueous lignosulfonate solution with a hydrophobic liquid, where the hydrophobic liquid comprises a pesticide active or agent (e.g., a pesticide liquid or a pesticide compound dissolved in an organic solvent) and forming the emulsion (e.g., by mechanical shear or ultrasonication); (c) drying the emulsion to form the pesticide composition. Optionally, the emulsion may comprise lactose, an inorganic salt, or other soluble material that may act as an inert filler.

The disclosed pesticide compositions may be prepared from aqueous emulsions. The prepared emulsions may comprise an active ingredient directly emulsified in water or an active ingredient dissolved in a solvent that is emulsified in water, and a lignosulfonate. In some embodiments, the disclosed emulsions comprise no more than about 50% (w/w) water (preferably no more than about 48% (w/w) water, more preferably no more than about 46% (w/w) water, even more preferably no more than about 44% (w/w) water).

The disclosed emulsions typically comprise lignosulfonate material. In some embodiments, the disclosed emulsions comprise no more than about 40% (w/w) of the lignosulfonate material (preferably no more than about 30% of the lignosulfonate material, more preferably no more than about 20% of the lignosulfonate material, even more preferably no more than about 10% of the lignosulfonate material).

In some embodiments, the disclosed emulsions include hydrophobic liquid droplets or particles having a relatively small size. For example, the disclosed emulsions may have a hydrophobic liquid droplet mean volume diameter of less than about 5 microns (preferably less than about 4 microns, more preferably less than about 3 microns even more preferably less than about 2 microns, 1 micron, or 0.6 microns).

The disclosed dry pesticide compositions may include granules or particles having a relatively small size. In some embodiments, the disclosed pesticide compositions may be used to prepare granular compositions, powder compositions, or a composition that comprises both granules and powder. Granular compositions may comprise granules having an average diameter of about 1 mm to about 8 mm (e.g., where granules represent at least about 80% of the total mass of the composition, preferably at least about 90% of the total mass of the composition, and more preferably at least about 95% of the total mass of the composition). Powder compositions may comprise solid particles having an average diameter of less than about 1 mm (e.g., where the solid particles represent at least about 80% of the total mass of the composition, preferably at least about 90% of the total mass of the composition, and more preferably at least about 95% of the total mass of the composition).

The disclosed methods for preparing the pesticide compositions may include a drying step (e.g., tray drying, belt drying, spray drying, and freeze drying). The disclosed methods for preparing the pesticide compositions may include a granulating step (e.g., fluid bed granulating).

In some embodiments, the granular pesticide composition or powder pesticide composition as disclosed herein may be combined or reconstituted with an aqueous solution to form an emulsion. An emulsion thus formed may include hydrophobic liquid droplets or particles having a relatively small size. For example, the disclosed reconstituted emulsions may include hydrophobic liquid droplets or particles having a mean volume diameter of less than about 5 microns (preferably less than about 4 microns, more preferably less than about 3 microns even more preferably less than about 2 microns, 1 micron, or 0.6 microns).

The disclosed compositions and methods may include or utilize a lignosulfonate that comprises sulfonated softwood lignin. The lignosulfonate may be prepared by methods that include acid sulfite pulping and optionally fermentation and optionally filtration to provide high purity, high molecular weight lignosulfonate. Fermentation may be performed to provide lignosulfonate having a low sugar content. Filtration may be performed to provide high molecular weight lignin sulfonate (e.g., filtration through a 20 kDa membrane cut-off filter, preferably through a 30 kDa membrane cut-off filter, more preferably through a 40 kDa membrane cut-off filter, even more preferably through a 50 kDa membrane cut-off filter).

The disclosed compositions and methods typically comprise or utilize high molecular weight softwood lignosulfonate. For example, the disclosed fluid emulsions may comprise about 15% (w/w) to about 35% (w/w) high purity, high molecular weight softwood lignosulfonate. The disclosed compositions also comprise a pesticide active or agent (e.g., as a liquid or compound). In some embodiments, the pesticide composition of the granules or powders may comprise at least about 40% (w/w) pesticide active (preferably at least about 50% (w/w) pesticide active, more preferably at least about 60% (w/w) pesticide active).

The disclosed compositions and methods may comprise or utilize a pesticide active (e.g., an herbicide, an insecticide, or a fungicide) which may be a liquid or solution (e.g., a pesticide compound dissolved in a solvent). Typically, the liquid or solution is hydrophobic (e.g., an organic or non-aqueous based liquid or a pesticide compound solubilized in an organic solvent). The pesticide active may include an agent selected from the group consisting of a thiocarbamate (e.g., ethyl dipropylthiocarbamate (EPTC); ethyl N,N-diisobutylthiocarbamate (butylate); S-ethyl N-ethylthiocyclohexanecarbamate (cycloate); S-Ethyl N,N-hexamethylenethiocarbamate (molinate); S-propyl dipropylthiocarbamate (vernolate), and mixtures thereof); a haloacetanilide (e.g., 2-Chloro-2'-methyl-6-ethyl-N-ethoxymethylacetanilide (acetochlor); 2-Ethyl-6-methyl-1-N-(2-methoxy-1-methylethyl)chloroacetanilide (metolachlor); 2-Chloro-2',6'-diethyl-N-(methoxymethyl)acetanilide (alachlor); 2',6'-Diethyl-N-butoxymethyl-2-chloroacetanilide (butachlor); 2-Chloro-N-isopropylacetanilide (propachlor); and mixtures thereof); a nitroaniline (e.g., 2,6-Dinitro-N,N-dipropyl-4-trifluoromethylaniline (trifluralin); 2,6-Dichloro-4-nitroaniline (dicloran); and mixtures thereof); an organophosphate (e.g., Diethyl 4-nitrophenyl phosphorothionate (parathion); S-(1,2-Di(ethoxycarbonyl)ethyl)dimethyl phosphorothiolothionate (malathion); O-Ethyl S-phenyl ethylphosphonothiolothionate (fonofos); and mixtures thereof); a pyrethroid (e.g., permethrin, lambda-cyhalothrin, deltamethrin, tralomethrin, cypermethrin, tefluthrin, and mixtures thereof); a strobilurin (e.g., azoxystrobin, kresoxim-methyl, picoxystrobin, fluoxastrobin, oryzastrobin, dimoxystrobin, pyraclostrobin, trifloxystrobin, and mixtures thereof); and mixtures thereof.

Lignosulfonate may function as an inert carrier, binding agent, or disintegrating agent in the disclosed compositions. Optionally, the disclosed compositions may include an additional inert carrier, binding agent, or disintegrating agent.

DETAILED DESCRIPTION

Disclosed are methods for producing powder or granular emulsifiable concentrate pesticide formulations. The disclosed pesticide formulations may be prepared from non-aqueous based liquid or solvent soluble pesticide actives using a high purity, high molecular weight sulfonated lignin as an emulsion stabilizer. When dried or granulated, the high purity, high molecular weight sulfonated lignin may provide an inert, water soluble matrix for the pesticide active. Upon reconstitution, the high purity, high molecular weight sulfonated lignin may function as an emulsion stabilizer for the pesticide.

Emulsions of the non-aqueous based liquid or solvent soluble pesticide actives may be reduced to a powder or granular form by any conventional drying or granulating method including but not limited to belt drying, tray drying, spray drying, freeze drying or fluid bed granulation. Preferably, tray drying is utilized. In the resulting granules, the high molecular weight sulfonated lignin may function as a solid matrix for the pesticide active.

The disclosed emulsifiable concentrate formulations thus formed, which may be dry granular emulsifiable concentrate formulations, typically have high loading rates, good storage properties, and good reconstitution properties when added to water. These properties typically are achieved via the use of a high purity, high molecular weight sulfonated lignin. Typically, the reconstituted emulsion has a superior stability in comparison to a similar product made with sulfonated lignins having lower purity and/or lower molecular weight.

The present invention is described herein using several definitions, as set forth below and throughout the application.

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the term "lignin" has its normal connotation, and refers to an amorphous polymer that occurs in woody material of higher plants such as trees. Lignin is composed of phenylpropanol groups (typically p-phenylpropanol groups) that are linked by various carbon-carbon linkages and ether linkages. Optionally, the phenyl moiety of the phenylpropanol group further is substituted by one or more methoxy groups adjacent to the phenyl moiety's hydroxyl group. The phenylpropanol groups of softwood lignin typically include fewer methoxy substitutions on the phenyl moiety (typically having one or no methoxy substitutions) than phenylpropanol groups of hardwood lignin (typically having two methoxy substitutions).

Lignin typically is recovered from the organosolve process, or from alkaline black pulping liquors such as are produced in the Kraft, soda, and other well known alkaline pulping operations. The term "sulfonated lignin," as used in this specification, refers to the product which is obtained by the introduction of sulfonic acid groups into the lignin molecule, as may be accomplished by the reaction of lignin with acid sulfite or bisulfite compounds. For example, the waste liquors from such organosolve or alkaline pulping contain large quantities of lignin and lignin decomposition products, which can be sulfonated or sulfomethylated by known processes, such as high temperature sulfonation, oxidative sulfonation at ambient temperature, or sulfomethylation by reaction of lignin, sodium sulfite and formaldehyde. As used herein, the term "sulfite lignin" refers to the reaction product of lignin, which is inherently obtained during sulfite pulping of wood, straw, corn stalks, bagasse and the like, and is a principle constituent of the spent sulfite liquor which is derived from that process. The phrases "lignosulfonate" and "lignin sulfonate" may be used interchangeably herein and include the sulfonated lignin and sulfite lignin reaction products described above, and also spent sulfite liquors that may be further reacted, purified, fractionated, or the like, as may be required to produce the lignosulfonate material of interest. The lignosulfonates may be utilized in the "as is" or whole liquor condition. They may also be utilized as a purified lignosulfonate material from, or in which the sugars and other saccharide constituents have been removed and/or destroyed, or additionally inorganic constituents have been partially or fully eliminated. Lignosulfonates may be utilized in their salt form. For example, calcium lignosulfonates, sodium lignosulfonates, ammonium lignosulfonates, potassium lignosulfonates, magnesium lignosulfonates and mixtures or blends thereof. Lignosulfonates are available from numerous sources in either solution or dried power forms.

In some embodiments, the above features and advantages may be accomplished by mixing a solution of a high purity, high molecular weight sulfonated lignin in water with a non-aqueous based liquid pesticide active or with an solvent-based solution of a pesticide active, generating a stable emulsion of the mixture using a high shear mixer and granulating the resulting emulsion via tray drying or fluid-bed granulation.

In some embodiments, the high purity, high molecular weight sulfonated lignin utilized herein may be prepared through the ultrafiltration of sulfonated lignins. The preferred ultrafiltration membrane may have a molecular size cut-off of at least about 20 kDa (preferably at least about 50 kDa). Preferably, the sulfonated lignins are sulfonated softwood lignin obtained from the sulfite pulping process. Preferably, the sulfonated lignins are fermented prior to ultrafiltration.

In some embodiments, the pesticide active may be a non-aqueous liquid or solution of a water insoluble active dissolved in a solvent or oil. Suitable solvents include but are not limited to oils, modified oils, petroleum distillates, mineral hydrocarbons, and chlorinated hydrocarbons. As disclosed herein, an "oil" is a hydrocarbon liquid that is not miscible with water. A "modified oil" is an oil that has been altered by fractionation, sulfomethylation, hydrogenation, halogenation, or other means to enhance certain end use properties, which may include, but are not limited to flash point temperature, melting temperature, hydrophobicity, and solvent properties. "Petroleum distillates" include petroleum distillation light fractions such as, but not limited to hexane, benzene, toluene, and xylene. "Mineral hydrocarbons" are hydrocarbons derived primarily from inorganic matter such as petroleum and generally are colorless, odorless, and tasteless, which, as disclosed herein, may be used as an adjuvant optionally with a surfactant to be applied in conjunction with a pesticide to improve application, longevity, or efficacy of the pesticide. "Chlorinated hydrocarbons" are hydrocarbons modified by chlorination such that they are nonflammable, noncorrosive, stable liquids, e.g., perchloroethane. "Crop oils" include vegetable oils, which, as disclosed herein, may be used as an adjuvant optionally with a surfactant to be applied in conjunction with a pesticide to improve application, longevity, or efficacy of the pesticide. "Modified crop oils" include liquid hydrocarbons suitable as crop adjuvants that have been modified to enhance or alter certain properties, such as but not limited to flash point temperature, melting temperature, hydrophobicity, and solvent properties (e.g., where methylation of soybean oil may enhance its ability to dissolve waxy plant cuticle).

In some embodiments, the initial emulsion concentrate formulation for drying is prepared by dissolving the high purity, high molecular weight lignin in the aqueous phase of the system. The non-aqueous liquid active or water insoluble active dissolved in a solvent is then emulsified into the aqueous lignin solution using a high shear emulsifying equipment, such as but not limited to a dispersator, rotor stator, ultrasonic mixer, and high pressure/high shear mixer. After the emulsion is formed, it may be belt-dried and broken into granules and/or it may be granulated using fluid bed technology. In other embodiments, the emulsion may be dried and/or granulated using procedures that include, but are not limited to spray drying, drum drying, and freeze drying.

In some embodiments, the emulsion, which optionally may be dried, may be granulated using wet granulation or dry granulation. Granulation procedures which may be utilized include, but are not limited to shear granulation, high-speed mixer granulation, fluidized-bed granulation, spray drying granulation, spheronizing or pelletizing by extrusion, rotor granulation, dry granulation tableting (e.g., using a slugger), and dry granulation using a roller compacter.

The pesticide compositions disclosed herein may include granule compositions and powder compositions. Typically, the granule compositions disclosed herein comprise granules having an average diameter that is at least about 1 millimeter and optionally no more than about 8 millimeters. The granules may have bulk properties similar to a semi-fluid where they exhibit flow through an orifice that is dependent on the size of the orifice rather than the pressure exerted by overhead material. As used herein, a "powder" is a loose aggregate of discrete particles of a dry material with maximum dimensions of less than 1 mm.

Emulsions comprising a pesticide active may be used to prepare pesticide compositions having a high loading rate of the pesticide active (e.g., granule compositions and powder compositions). "Loading rate" may be defined as the percentage (w/w) of the active in the final dry pesticide composition. The disclosed granular compositions and powder compositions typically have a high loading rate where levels of pesticide active loading in the granules and powders may be at least about 40%, 50% or 60% (e.g., where the pesticide active is a liquid). The percentage of pesticide active in a granule composition or powder composition may vary where the pesticide active is present as a percent solution in an emulsion used to form the granule composition or powder composition. For example, the emulsion may comprise a pesticide active as a percent solution of a pesticide compound dissolved in an organic solvent (or optionally as a pesticide liquid mixed with another organic liquid). In this case, the loading rate will vary based on the concentration of the pesticide active in the percent solution used to form the emulsion.

The disclosed compositions and methods may utilize or include high purity sulfonated lignin. As disclosed herein, a "high purity sulfonated lignin" is a sulfonated lignin in which contaminants such as sugars and phenolic monomers and oligomers (e.g., polymers having fewer than about 10 monomers) have been removed such that at least about 90% of the dry matter is composed of sulfonated lignin salt. Optionally, high purity sulfonated lignin may be obtained by performing methods that include fermenting and/or ultrafiltering. Purity may be assessed by determining methoxyl content of the lignosulfonate material. In some embodiments, the methoxyl content of lignosulfonate salt may be measured and corrected for the weight of the associated sulfonic groups and salt cation to calculate the purity of the sulfonated lignin salt using the typical methoxyl content of lignin in the calculation (e.g., about 14.6% methoxyl content).

The disclosed compositions and methods may utilize or include high molecular weight sulfonated lignin. As disclosed herein, a "high molecular weight sulfonated lignin" typically has a molecular weight that is greater than about 20 kDa (preferably greater than about 30 kDa, more preferably greater than about 40 kDa, and even more preferably greater than about 50 kDa), which optionally may be determined by size exclusion chromatography (SEC) and/or multi-angle laser light scattering (MALLS).

The disclosed composition and methods may utilize or include pesticide actives. As disclosed herein, a "pesticide active" may include but is not limited to non-aqueous pesticide liquids or pesticide compounds which optionally are dissolved in non-aqueous solvents (e.g., organic solvents) as a pesticide solution. Pesticides may include, but are not limited to herbicides, insecticides, and fungicides. Oil-soluble, water-insoluble pesticides may include, but are not limited to thiocarbamate herbicides such as EPTC, butylate, cycloate, molinate, and vernolate; haloacetanilide herbicides such as acetochlor, metoachlor, alachlor, butachlor, and propachlor; nitroaniline herbicides such as trifluralin; organophosphorus insecticides such as parathion, malthion, and fonofos; pyrethroid insecticides such as permethrin, lambda-cyhalothrin, deltamethrin, tralomethrin, cypermethrin, and tefluthrin; and fungicides such as azoxystrobin.

The disclosed pesticide compositions may be made from emulsions formed by combining aqueous solutions with non-aqueous based liquids or solvent based solutions. As disclosed herein, "non-aqueous based liquids" and "solvent based solutions" include organic, non-polar liquids capable of dissolving organic molecules which are insoluble in water. Examples include, but are not limited to, Aromatic 150, which is a petroleum derived hydrocarbon solvent that may be used to dissolve a solid form of acetochlor or to dilute a liquid form of acetochlor.

The disclosed compositions may include inert fillers, carriers, binding agents, and/or disintegrating agents. Inert carriers include, but are not limited to sugars (e.g., lactose), starch, and kaolin. Inert binders may include, but are not limited to sugars (e.g., lactose), starch, and natural and synthetic gums. Inert disintegrators may include, but are not limited to starch, agar, bentonite, and cellulose.

The disclosed compositions may exhibit desirable properties after storage. For example, granular pesticide composition as disclosed herein may be stored for greater than about 1, 2, or 3 months at a temperature of about 22° C., 40° C., or 45° C. The stored granular pesticide composition may exhibit one or more desirable properties selected from the group consisting of desirable flowability or lack of caking, desirable dispersibility in water or "bloom," and desirable stability of an emulsion formed from the stored granular pesticide composition.

The disclosed compositions may exhibit desirable stability properties. For example, the disclosed compositions may exhibit desirable stability properties after storage (e.g., for a period of time such as 15 minutes, 30 minutes, 1 hour, 2 hours, 4 hours, 8 hours, 1 day, 1 week, 1 month, 2 months, 3 months, 1 year, or longer periods of time). In some embodiments, the disclosed compositions may include emulsions that exhibit desirable stability, for example, where the disclosed emulsions remain uniform and homogeneous without evidence of gravitational separations or particle agglomeration or coalescence after the emulsion is stored for a period of time. The disclosed emulsions also may exhibit desirable stability where the emulsion comprises emulsified oil droplets (i.e., particles) having a size distribution that remains substantially constant after procedures that include drying, storage, and redissolving. The disclosed compositions may include granules that exhibit desirable stability properties, for example, where after storage the granules remain distinct, separate, and semifluid (i.e., non-agglomerated). The disclosed compositions also may include granules that exhibit desirable stability properties related to chemical properties, for example, where after storage the chemical properties of the granules remain substantially unchanged. In some embodiments, disclosed granules include a surfactant matrix which remains water soluble and capable of stabilizing an emulsion after the granules are stored for a period of time.

In further embodiments of the pesticide compositions, the pesticide activity of a pesticide active in an emulsion composition is not substantially reduced after the emulsion is dried and reconstituted to form a second emulsion. For example, in some embodiments the pesticide active may retain at least about 80% of its pesticide activity after reconstitution (preferably at least about 90% of its pesticide activity after reconstitution, and more preferably at least about 95% of its pesticide activity after reconstitution). In addition, the pesticide activity of a pesticide active in the disclosed compositions may retain at least about 80%, 90%, or preferably 95% of its pesticide activity after storage (e.g., after 1 day, 1 week, 1 month, 3 months, 1 year, or longer) at a selected temperature (e.g., 4° C., 20° C., 22° C., 45° C., or 54° C.). In some embodiments, "pesticide activity" may be measured as the pesticide's effective concentration for killing 50% of a target pest population or $EC_{50}$.

In even further embodiments, the granules may exhibit reduced hygroscopicity in comparison to granules prepared from sulfonated lignins having lower purity and/or lower molecular weight. In still even further embodiments, the granules may exhibit more rapid dissolution in an aqueous solution in comparison to granules prepared from sulfonated lignins having lower purity and/or lower molecular weight (e.g., sulfonated lignins not subjected to fermentation and/or filtering) and/or from sulfonated lignins that are not in a sodium salt form. For example, in some embodiments of the granular compositions, greater than about 95% of the granules are solubilized in water after no more than about 1 minute (preferably greater than about 99% of the granules are solubilized in water after no more than about 1 minute).

ILLUSTRATIVE EMBODIMENTS

The following embodiments are illustrative and are not intended to limit the disclosed subject matter.

Embodiment 1

A method for preparing a pesticide composition, the method comprising: (a) preparing an aqueous lignosulfonate solution by dissolving a lignosulfonate material in water or an aqueous solution, wherein the lignosulfonate material comprises at least about 90% (w/w) lignosulfonate and the lignosulfonate has an average molecular weight of about 20 kDa to about 100 kDa; (b) combining the aqueous lignosulfonate solution with a hydrophobic liquid, wherein the hydrophobic liquid comprises a pesticide active or a pesticide compound dissolved in an organic solvent, and forming an emulsion (e.g., by mechanical shear or ultrasonication); (c) drying the emulsion to form the pesticide composition.

Embodiment 2

In some embodiments, the disclosed emulsions include hydrophobic liquid droplets or particles having a relatively small size. For example, the disclosed emulsions may have a hydrophobic liquid droplet mean volume diameter of less than about 5 microns (preferably less than about 4 microns, more preferably less than about 3 microns, even more preferably less than about 2 microns, 1 micron, 0.8 microns, 0.6 microns, or 0.4 microns).

Embodiment 3

The method of embodiment 1 or 2, wherein the pesticide composition is a granular composition comprising granules having an average diameter of about 1 mm to about 8 mm.

Embodiment 4

The method of any of embodiments 1-3, wherein the pesticide composition is a powder composition comprising particles having an average diameter of less than 1 mm.

Embodiment 5

The method of any of embodiments 1-4, wherein drying is performed by a method selected from the group consisting of tray drying, belt drying, spray drying, and freeze drying.

Embodiment 6

The method of any of embodiments 1-5, further comprising granulating the pesticide composition to form a granular composition comprising granules having an average particle diameter of about 1 mm to about 8 mm.

Embodiment 7

The method of embodiment 6, wherein granulating is performed by fluid bed granulating.

Embodiment 8

The method of any of embodiments 1-7, further comprising: (d) combining the pesticide composition with a second aqueous solution or water to form a second emulsion.

Embodiment 9

The method of embodiment 8, wherein the second emulsion comprises hydrophobic droplets or particles having a mean volume diameter of less than about 5 microns (preferably less than about 4 microns, more preferably less than about 3 microns, even more preferably less than about 2 microns, 1 micron, 0.8 microns, 0.6 microns, or 0.4 microns).

Embodiment 10

The method of any of embodiments 1-9, wherein the lignosulfonate comprises sulfonated softwood lignin.

Embodiment 11

The method of any of embodiments 1-10, wherein the lignosulfonate material comprises at least about 95% (w/w) lignosulfonate.

Embodiment 12

The method of any of embodiments 1-11, wherein the lignosulfonate has an average molecular weight of about 40 kDa to about 60 kDa.

Embodiment 13

The method of any of embodiments 1-12, wherein the emulsion comprises no more than about 40% (w/w) lignosulfonate.

Embodiment 14

The method of any of embodiments 1-13, wherein the dry pesticide composition comprises at least about 40%, 50%, or 60% (w/w) pesticide active.

Embodiment 15

The method of any of embodiments 1-14, wherein the pesticide active or compound comprises an agent from the group consisting of a thiocarbamate, a haloacetanilide, a nitroaniline, an organophosphorus, a pyrethroid, a strobilurin, and mixtures thereof.

Embodiment 16

The method of embodiment 15, wherein the thiocarbamate is selected from the group consisting of ethyl dipropylthiocarbamate (EPTC); ethyl N,N-diisobutylthiocarbamate (butylate); S-ethyl N-ethylthiocyclohexanecarbamate (cycloate); S-Ethyl N,N-hexamethylenethiocarbamate (molinate); S-propyl dipropylthiocarbamate (vernolate); and mixtures thereof.

Embodiment 17

The method of embodiment 15, wherein the haloacetanilide is selected from the group consisting of 2-Chloro-2'-methyl-6-ethyl-N-ethoxymethylacetanilide (acetocholor); 2-Ethyl-6-methyl-1-N-(2-methoxy-1-methylethyl)chloroacetanilide (metolachlor); 2-Chloro-2',6'-diethyl-N-(methoxymethyl)acetanilide (alachlor); 2',6'-Diethyl-N-butoxymethyl-2-chloroacetanilide (butachlor); 2-Chloro-N-isopropylacetanilide (propachlor); and mixtures thereof.

Embodiment 18

The method of embodiment 15, wherein the nitroaniline is selected from the group consisting of 2,6-Dinitro-N,N-dipropyl-4-trifluoromethylaniline (trifluralin); 2,6-Dichloro-4-nitroaniline (dicloran); and mixtures thereof.

Embodiment 19

The method of embodiment 15, wherein the organophosphate is selected from the group consisting of Diethyl 4-nitrophenyl phosphorothionate (parathion); S-(1,2-Di(ethoxycarbonyl)ethyl)dimethyl phosphorothiolothionate (malathion); O-Ethyl S-phenyl ethylphosphonothiolothionate (fonofos); and mixtures thereof.

Embodiment 20

The method of embodiment 15, wherein the pyrethroid is selected from the group consisting of permethrin, lambda-cyhalothrin, deltamethrin, tralomethrin, cypermethrin, tefluthrin, and mixtures thereof.

Embodiment 21

The method of embodiment 15, wherein the strobilurin is selected from the group consisting of azoxystrobin, kresoxim-methyl, picoxystrobin, fluoxastrobin, oryzastrobin, dimoxystrobin, pyraclostrobin, trifloxystrobin, and mixtures thereof.

Embodiment 22

A pesticide composition prepared by the method of any of embodiments 1-21.

Embodiment 23

A method for preparing a granular pesticide composition, the method comprising: (a) preparing an aqueous lignosulfonate solution by dissolving a lignosulfonate material in water or an aqueous solution, wherein the lignosulfonate material comprises at least about 90% (w/w) lignosulfonate and the lignosulfonate has an average molecular weight of about 20 kDa to about 100 kDa; (b) combining the aqueous lignosulfonate solution with a hydrophobic liquid, wherein the hydrophobic liquid comprises a pesticide active or a pesticide compound dissolved in an organic solvent, and forming an emulsion (e.g., by mechanical shear or ultrasonication); (c) granulating the emulsion to obtain the granule pesticide composition, wherein the composition comprises granules having an average particle diameter of about 1 mm to about 8 mm.

Embodiment 24

The method of embodiment 23, wherein the lignosulfonate comprises sulfonated softwood lignin.

Embodiment 25

The method of embodiment 23 or 24, wherein the lignosulfonate material comprises at least about 95% (w/w) lignosulfonate.

Embodiment 26

The method of any of embodiments 23-25, wherein the lignosulfonate has an average molecular weight of about 40 kDa to about 60 kDa.

Embodiment 27

The method of any of embodiments 23-26, wherein the granules comprise at least about 40%, 50%, or 60% (w/w) pesticide active.

Embodiment 28

The method of any of embodiments 23-27, wherein the pesticide active comprises an agent selected from the group consisting of a thiocarbamate, a haloacetanilide, a nitroaniline, an organophosphorus, a pyrethroid, a strobilurin, and mixtures thereof.

Embodiment 29

The method of embodiment 28, wherein the thiocarbamate is selected from the group consisting of ethyl dipropylthiocarbamate (EPTC); ethyl N,N-diisobutylthiocarbamate (butylate); S-ethyl N-ethylthiocyclohexanecarbamate (cycloate); S-Ethyl N,N-hexamethylenethiocarbamate (molinate); S-propyl dipropylthiocarbamate (vernolate); and mixtures thereof.

Embodiment 30

The method of embodiment 28, wherein the haloacetanilide is selected from the group consisting of 2-Chloro-2'-methyl-6-ethyl-N-ethoxymethylacetanilide (acetocholor); 2-Ethyl-6-methyl-1-N-(2-methoxy-1-methylethyl)chloroacetanilide (metolachlor); 2-Chloro-2',6'-diethyl-N-(methoxymethyl)acetanilide (alachlor); 2',6'-Diethyl-N-butoxymethyl-2-chloroacetanilide (butachlor); 2-Chloro-N-isopropylacetanilide (propachlor); and mixtures thereof.

Embodiment 31

The method of embodiment 28, wherein the nitroaniline is selected from the group consisting of 2,6-Dinitro-N,N-dipropyl-4-trifluoromethylaniline (trifluralin); 2,6-Dichloro-4-nitroaniline (dicloran); and mixtures thereof.

Embodiment 32

The method of embodiment 28, wherein the organophosphorus is selected from the group consisting of Diethyl 4-nitrophenyl phosphorothionate (parathion); S-(1,2-Di(ethoxycarbonyl)ethyl)dimethyl phosphorothiolothionate (malathion); O-Ethyl S-phenyl ethylphosphonothiolothionate (fonofos); and mixtures thereof.

Embodiment 33

The method of embodiment 28, wherein the pyrethroid is selected from the group consisting of permethrin, lambda-cyhalothrin, deltamethrin, tralomethrin, cypermethrin, tefluthrin, and mixtures thereof.

Embodiment 34

The method of embodiment 28, wherein the strobilurin is selected from the group consisting of azoxystrobin, kresoxim-methyl, picoxystrobin, fluoxastrobin, oryzastrobin, dimoxystrobin, pyraclostrobin, trifloxystrobin, and mixtures thereof.

Embodiment 35

A granular pesticide composition prepared by the method of any of embodiments 23-34.

Embodiment 36

A pesticide composition prepared from an emulsion comprising: (a) 15-50% (w/w) water (or 35-50% or 40-45% (w/w) water); (b) 15-35% (w/w) lignosulfonate material (or 20-30% lignosulfonate material), wherein the lignosulfonate material comprises at least about 90% (w/w) softwood lignosulfonate having an average molecular weight of about 40 kDa to about 60 kDa; and (c) 15-45% (w/w) pesticide active (or 20-40% w/w) pesticide active), wherein the pesticide active is a hydrophobic liquid; wherein the emulsion comprises hydrophobic droplets or particles having a mean volume diameter of less than about 5 microns (preferably less than about 4 microns, more preferably less than about 3 microns, even more preferably less than about 2 microns, 1 micron, 0.8 microns, 0.6 microns, or 0.4 microns).

EXAMPLES

The following examples are illustrative and are not intended to limit the disclosed subject matter.

Example I

Granular Emulsifiable Concentrate Formulation A

In this example, canola oil was used as a substitute for a pesticide active. Forty grams of Ultrazine NA, a high purity, high molecular weight lignosulfonate available from Borregaard LignoTech were dissolved in sixty (60) grams of water. Forty grams of canola oil were then added and an emulsion was formed by mixing in a Waring blender on high speed for five (5) minutes. The resulting emulsion, which had an average oil droplet mean volume diameter of less than one micron size, was then poured onto a glass tray and oven dried at 105° C. for (15) minutes. After breaking the resulting dried sheet into −6 by +20 mesh particles, five (5) grams of the resulting granules were re-mixed into 10 grams of water to form a second stable emulsion with an average droplet mean volume diameter of less than one micron.

Example II

Granular Emulsifiable Concentrate Formulation B

In this example, a non-aqueous liquid acetochlor herbicide was used as the pesticide active. Twenty-five grams of Ultrazine NA, a high purity, high molecular weight lignosulfonate available from Borregaard LignoTech was dissolved in 75 grams of water. Twenty-five grams of acetochlor was then added and an emulsion was formed by mixing in a Waring blender on high speed for five (5) minutes. The resulting emulsion, which had an average oil droplet size of about two (2) microns, was then poured onto a glass tray to a thickness of about 1-2 mm and allowed to dry at room temperature to a form a solid containing 50% (w/w) acetochlor. After breaking the resulting dried sheet into −6 by +20 mesh particles, five (5) grams of the resulting granules were re-mixed into ten (10) grams of water to form a second stable emulsion with an average droplet size of two (2) microns. A second formulation was prepared similarly in which acetochlor was present at a concentration of 60% (w/w) in the dry product.

The resulting dry granules were stored for three months at 22° C., 40° C., and 54° C. The granules remained free-flowing after storage except for the product having 60% (w/w) acetochlor which exhibited slight caking after having been stored at 54° C. This product returned to discrete granular form upon cooling and mild shaking. All products dissolved rapidly in water and formed a homogenous emulsion within about sixty (60) seconds.

Example III

Powder Emulsifiable Concentrate Formulation A

In this example, Soygold 2500, crop oil supplied by Ag Environmental Products, was used as a substitute pesticide active. Twenty-five (25) grams of Ultrazine NA, a high purity, high molecular weight lignosulfonate available from Borregaard LignoTech was dissolved in seventy-five (75) grams of water. Twenty-five (25) grams of Soygold 2500 was then added and an emulsion was formed by mixing in a Waring blender on high speed for three (3) minutes. The resulting emulsion, which had an average oil droplet size of about two (2) microns, was then spray dried in a Yamato ADL31 lab spray dryer. Five grams (5) of the resulting powder were re-mixed into ten (10) grams of water to form a second stable emulsion with an average droplet size of two (2) microns.

Example IV

Powder Emulsifiable Concentrate Formulation B

In this example, canola oil was used as a substitute pesticide active. Twenty-five grams of Ultrazine NA, a high purity, high molecular weight lignosulfonate available from Borregaard LignoTech was dissolved in seventy-five (75) grams of water. Twenty-five (25) grams of canola oil was then added and an emulsion was formed by mixing in a Waring blender on high speed for three (3) minutes. The resulting emulsion, which had an average oil droplet size of about two (2) microns, was then freeze dried in a freeze dryer. Five (5) grams of the resulting powder were re-mixed into ten (10)

grams of water to form a second stable emulsion with an average droplet size of two (2) microns.

Example V

Particle Size Analysis

Ten different emulsions were prepared which contained differing amounts of water; high-purity, high molecular weight lignosulfonate material; and oil. (See formulations in Table 1.) Water was added to a 250 mL Waring blender cup. The blender was turned on low speed and Ultrazine NA was sifted into the water and allowed to dissolve for one minute. Oil was then added as a substituted pesticide active and the blender speed was increased to high for five (5) minutes to form an emulsion. The resulting emulsion was bottled for storage.

Approximately nine (9) grams of the emulsion was spread on a glass plate over an area of about 120 cm. The plate was placed in a 105° C. forced air oven for fifteen (15) minutes, after which the plate was removed and allowed to cool. The dry film was removed from the plate with a razor blade to form a free-flowing granular composition. This composition could be dissolved in water to form a second, reconstituted emulsion. Particle size analysis for the original and reconstituted emulsions was performed on a MicroTrac X100 with a pump speed of 10. Results are provided in Table 1.

TABLE 1

| | Formulation (g) | | | Water | Oil | Particle size (μm) | |
|---|---|---|---|---|---|---|---|
| Prep | Water | UNA | Oil | % of total | % of dry | Liquid | Dry |
| 1 | 75 | 25 | 25 | 60.0 | 50 | 2.1 | 9.2 |
| 2 | 75 | 25 | 25 | 60.0 | 50 | 2.0 | 5.0 |
| 3 | 60 | 25 | 25 | 54.5 | 50 | 1.2 | 3.5 |
| 4 | 60 | 30 | 30 | 50.0 | 50 | 0.7 | 3.4 |
| 5 | 60 | 30 | 45 | 44.4 | 60 | 0.6 | 3.2 |
| 6 | 60 | 30 | 30 | 54.5 | 40 | 0.7 | 1.3 |
| 7 | 60 | 30 | 60 | 40.0 | 67 | 0.8 | 2.8 |
| 8 | 60 | 40 | 40 | 42.9 | 50 | 0.3 | 0.8 |
| 9 | 75 | 30 | 45 | 50.0 | 60 | 1.0 | 6.1 |
| 10 | 60 | 36 | 24 | 50.0 | 40 | 0.4 | 0.7 |

With respect to the original emulsions, preparation nos. 1 & 2 were stable overnight but exhibited separation after two weeks, where a cream layer was observed to form on the top of the emulsion. Preparation 3 exhibited separation to a lesser degree. None of the other preparations exhibited any signs of separation after two weeks storage at room temperature. When 50% or less water is used to form the emulsion, the preparation is observed to remain stable long enough for the drying process to be achieved without difficulty. For preparations having equal amounts of oil and Ultrazine, increasing the amount of water had a small effect on particle size for the original emulsions but had a larger effect on particle size for the reconstituted emulsions. For preparations having water held constant at 50%, increasing the amount of oil also led to a small increase in particle size for the original emulsions but had a larger effect on particle size for the reconstituted emulsions.

The invention claimed is:

1. A method for preparing a dried pesticide composition, the method comprising:
   (a) preparing an aqueous lignosulfonate solution by dissolving a lignosulfonate material in water or an aqueous solution, wherein the lignosulfonate material comprises at least 90% (w/w) softwood lignosulfonate and the softwood lignosulfonate has an average molecular weight of 40 kDa to 100 kDa;
   (b) combining the aqueous lignosulfonate solution with a hydrophobic liquid and forming an emulsion, wherein the hydrophobic liquid comprises a pesticide active; and
   (c) drying the emulsion to remove the water and to form the dried pesticide composition in a granular form.

2. The method of claim 1, wherein forming the emulsion comprises subjecting the combined aqueous lignosulfonate solution and hydrophobic liquid to mechanical shear.

3. The method of claim 1, wherein the hydrophobic liquid comprises a pesticide compound dissolved in an organic solvent.

4. The method of claim 1, wherein the emulsion comprises hydrophobic droplets or particles having a mean volume diameter of less than about 5 microns.

5. The method of claim 1, wherein the dried pesticide composition is a granular composition comprising granules having an average diameter of about 1 mm to about 8 mm.

6. The method of claim 1, wherein the dried pesticide composition is a powder composition comprising particles having an average diameter of less than 1 mm.

7. The method of claim 1, further comprising granulating the dried pesticide composition to form a granular composition comprising granules having an average particle diameter of about 1 mm to about 8 mm.

8. The method of claim 1, further comprising:
   (d) combining the dried pesticide composition with water or a second aqueous solution to form a second emulsion.

9. The method of claim 8, wherein the second emulsion comprises hydrophobic droplets or particles having a mean volume diameter of less than about 5 microns.

10. The method of claim 1, wherein the lignosulfonate material comprises at least about 95% (w/w) softwood lignosulfonate.

11. The method of claim 1, wherein the softwood lignosulfonate has an average molecular weight of about 40 kDa to about 60 kDa.

12. The method of claim 1, wherein the emulsion comprises about 15% (w/w) softwood lignosulfonate to about 35% (w/w) softwood lignosulfonate.

13. The method of claim 1, wherein the pesticide active comprises an agent selected from the group consisting of a thiocarbamate, a haloacetanilide, a nitroaniline, an organophosphate, a pyrethroid, a strobilurin, and mixtures thereof.

14. The method of claim 13, wherein the thiocarbamate is selected from the group consisting of ethyl dipropylthiocarbamate (EPIC); ethyl N,N-diisobutylthiocarbamate (butylate); S-ethyl N-ethylthiocyclohexanecarbamate (cycloate); S-Ethyl N,N-hexamethylenethiocarbamate (molinate); S-propyl dipropylthiocarbamate (vernolate); and mixtures thereof.

15. The method of claim 13, wherein the haloacetanilide is selected from the group consisting of 2-Chloro-2'-methyl-6-ethyl-N-ethoxymethylacetanilide (acetochlor); 2-Ethyl-6-methyl-1-N-(2-methoxy-1-methylethyl)chloroacetanilide (metolachlor); 2-Chloro-2',6'-diethyl-N-(methoxymethyl)acetanilide (alachlor); 2',6'-Diethyl-N-butoxymethyl-2-chloroacetanilide (butachlor); 2-Chloro-N-isopropylacetanilide (propachlor); and mixtures thereof.

16. The method of claim 13, wherein the nitroaniline is selected from the group consisting of 2,6-Dinitro-N,N-dipropyl-4-trifluoromethylaniline (trifluralin); 2,6-Dichloro-4-nitroaniline (dicloran); and mixtures thereof.

17. The method of claim 13, wherein the organophosphate is selected from the group consisting of Diethyl 4-nitrophenyl phosphorothionate (parathion); S-(1,2-Di(ethoxycarbonyl) ethyl) dimethyl phosphorothiolothionate (malathion); O-Ethyl S-phenyl ethylphosphonothiolothionate (fonofos); and mixtures thereof.

18. The method of claim 13, wherein the pyrethroid is selected from the group consisting of permethrin, lambda-cyhalothrin, deltamethrin, tralomethrin, cypermethrin, tefluthrin, and mixtures thereof.

19. The method of claim 13, wherein the strobilurin is selected from the group consisting of azoxystrobin, kresoxim-methyl, picoxystrobin, fluoxastrobin, oryzastrobin, dimoxystrobin, pyraclostrobin, trifloxystrobin, and mixtures thereof.

20. A method for preparing a granular pesticide composition, the method comprising:
(a) preparing an aqueous lignosulfonate solution by dissolving a lignosulfonate material in water or an aqueous solution, wherein the lignosulfonate material comprises at least 90% (w/w) softwood lignosulfonate having an average molecular weight of about 40 kDa to about 60 kDa;
(b) combining the aqueous lignosulfonate solution with a hydrophobic liquid and forming an emulsion, wherein the hydrophobic liquid comprises a pesticide active; and
(c) drying and granulating the emulsion to obtain the granular pesticide composition, wherein the granular pesticide composition comprises granules having an average particle diameter of about 1 mm to about 8 mm.

21. The method of claim 20, wherein forming the emulsion comprises subjecting the combined aqueous lignosulfonate solution and the hydrophobic liquid to mechanical shear.

22. The method of claim 1, wherein the emulsion comprises 15-45% (w/w) of the hydrophobic liquid.

23. The method of claim 20, wherein the emulsion comprises 15-45% (w/w) of the hydrophobic liquid.

24. The method of claim 1, wherein the emulsion comprises 20-40% (w/w) of the hydrophobic liquid.

25. The method of claim 20, wherein the emulsion comprises 20-40% (w/w) of the hydrophobic liquid.

26. The method of claim 1, wherein the emulsion comprises hydrophobic droplets or particles having a mean volume diameter of less than about 2 microns.

27. The method of claim 20, wherein the emulsion comprises hydrophobic droplets or particles having a mean volume diameter of less than 2 microns.

28. The method of claim 1, wherein after the dried pesticide composition is combined with water, the dried pesticide composition forms a second emulsion.

29. The method of claim 28, wherein the second emulsion comprises hydrophobic droplets or particles having a mean volume diameter of less than 5 microns.

30. The method of claim 20, wherein after the granulated pesticide composition is combined with water, the granulated pesticide composition forms a second emulsion.

31. The method of claim 30, wherein the second emulsion comprises hydrophobic droplets or particles having a mean volume diameter of less than 5 microns.

* * * * *